(12) United States Patent
Scheuer et al.

(10) Patent No.: US 6,274,551 B1
(45) Date of Patent: Aug. 14, 2001

(54) CYTOTOXIC AND ANTIVIRAL COMPOUND

(75) Inventors: Paul J Scheuer; Mark T Hamann, both of Honolulu, HI (US); Dolores G. Gravalos, Madrid (ES)

(73) Assignee: PharmaMar, S.A., Madrid (ES)

( * ) Notice: Subject to any disclaimer, the term of this patent is extended or adjusted under 35 U.S.C. 154(b) by 0 days.

(21) Appl. No.: 08/192,569

(22) Filed: Feb. 3, 1994

(51) Int. Cl.$^7$ ............... A61K 38/12; C07K 7/64

(52) U.S. Cl. ............... 514/9; 530/321; 530/317; 514/9; 514/2; 930/DIG. 546; 930/DIG. 548

(58) Field of Search ............... 530/317, 321; 514/11, 9, 2; 930/DIG. 546, DIG. 548

(56) References Cited

PUBLICATIONS

*UMI Dissertation Services*, "Biologically Active Constituents of Some Marine Invertebrates", Hamaii, Mark Todd, Ph.D., University of Hawaii, 1992.
Hamann et al, J. Am. Chem. Soc., 115, pp. 5825–5826 (1993).
Merck Manual, 11$^{th}$ ed., pp. 761–763; 1368–1371; pp. 456–459.

*Primary Examiner*—Keith D. MacMillan
*Assistant Examiner*—T. D. Wessendorf

(74) *Attorney, Agent, or Firm*—Ernest V. Linek; Banner & Witcoff, Ltd.

(57) ABSTRACT

Kalahide F, of formula I below, may be isolated from a sacoglossan. The compound may be used in the manufacture of pharmaceutical compositions or in the treatment of tumors or viral conditions.

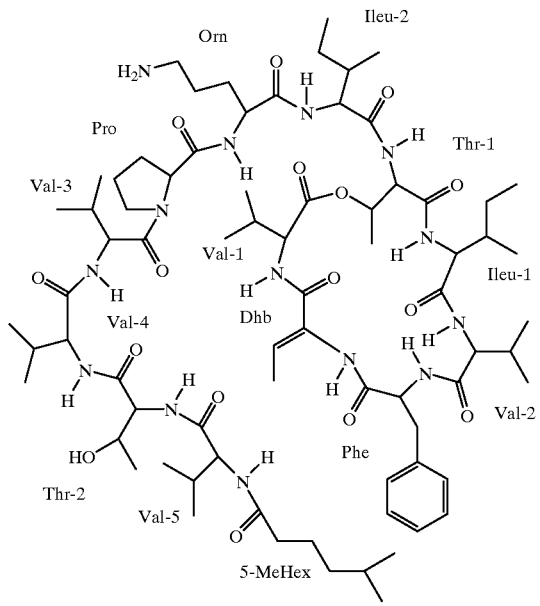

10 Claims, No Drawings

CYTOTOXIC AND ANTIVIRAL COMPOUND

This invention is concerned with a cytotoxic and antiviral compound isolated from the sacoglossan, *Elysia rafescens*.

According to the invention there is provided, a new compound, the peptide, Kahalalide F, of the formula:

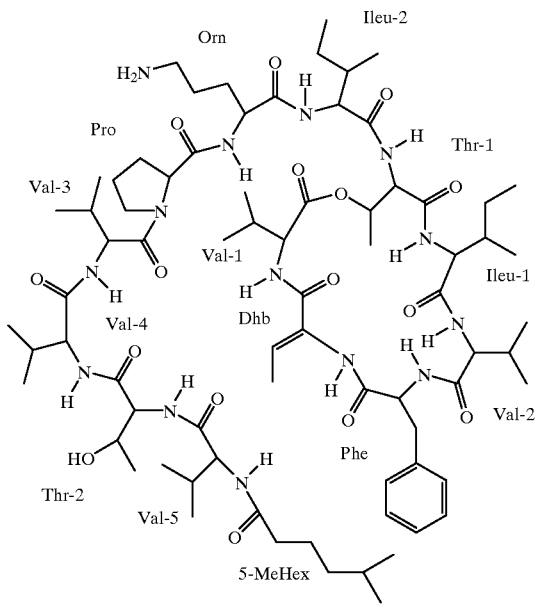

The antitumor activities of this compound has been determined "in vitro" in cell cultures of human lung carcinoma A-549 and human colon carcinoma HT-29. The procedure was carried out using the metnhodology described by Raymond J. Bergeron et al. *Biochem. Bioph. Res. Comm.* 1984, 121(3), 848–854 and by Alan C. Schroeder et al. *J. Med. Chem.* 1981, 24 1078–1083.

The antiviral activities of this compound have also been determined "in vitro" against HSV (Herpes simplex virus) and VSV (Vesicular stomatitis virus). The methodology used to carry out this determination is described by Raymond J. Bergeron et al. *Biochem. Bioph. Res. Comm.* 1984, 121(3), 848–854 and by Alan C. Schroeder et al. *J. Med. Chem.* 1981, 24 1078–1083.

Therefore, the present invention also provides a method of treating any mammal affected by a malignant tumor sensitive to compounds above described, which comprises administering to the affected individual a therapeutically effective amount of these compounds or a pharmaceutical composition thereof; and a method of treating viral infections in mammals, comprising administering to a patient in need of such treatment, an antiviral effective amount of the compounds described in the present invention.

The present invention also relates to pharmaceutical preparations which contain as active ingredient these compounds, or a pharmaceutically acceptable acid addition salt thereof, as well as the process for its preparation.

Examples of pharmaceutical compositions include any solid (tablets, pills, capsules, granules, etc.) or liquid (solutions, suspensions or emulsions) suitable composition for oral, topical or parenteral administration, and they may contain the pure compound or in combination with any carrier or other pharmacologically active compounds. These compositions may need to be sterile when administered parenterally.

The correct dosage of a pharmaceutical composition of these compounds will vary according to the particular formulation, the mode of application and particular site, host and tumor being treated. Other factors like age, body weight, sex, diet, time of administration, rate of excretion, condition of the host, drug combinations, reaction sensitivities and severity of disease shall be taken in account. Administration can be carried out continuously or periodically within the maximum tolerated dose. Kahalalide F was isolated from the sacoglossan, Elysia rufescens (family Plakobranchidae, order Sacoglossa), collected near Black point, Oahu. This animal varies in size between 1 and 4 cm; it is dark red-brown in color with light-colored spots. There is orange fringing of the parapodia, which have very small dark green spots from sequestered chloroplasts. *Elysia rufescens* feeds on the delicate, feather-like green alga Bryopsis sp.[1] Kahalalide F can also be isolated from this alga. Two hundred animals were collected over the period of several weeks during spring, 1991 and extracted with EtOH. The extracts were then chromatographed by silica gel flash chromatography (hexane, hexane/EtOAc (1:1), EtOAc, EtOAc (1:1), MeOH and MeOH/HOAc (98:2). The peptides were eluted with EtOAc/MeOH (1:1). Final purification was accomplished by repeated HPLC (RP C18) using MeCN/$H_2O$ with 0.1% TFA (70–45% $H_2O$).

ISOLATION SCHEME

*Elysia rufescens*

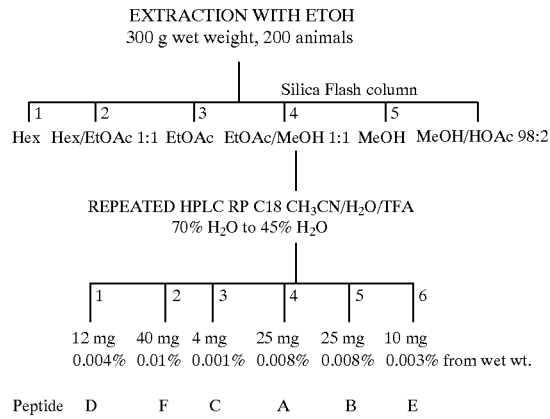

The structures of the peptides were elucidated by 2D NMR experiments (HMQC, HMBC, TOCSY, COSY and ROESY).

Kahalalide F was isolated as a white amorphous powder in 0.02% yield. A molecular formula of $C_{75}H_{124}N_{14}O_{16}$ was deduced from detailed analyses of the $^{13}C$ and $^1H$ NMR spectra and the high resolution FAB mass spectrum. The 14 substructures in this compound arise from five valines, two isoleucines, two threonines, ornithine, dehydroaminobutyric acid. proline, phenilalanine and 5-methythexanoic acid (5-MeHex). Kahalalide F is the largest peptide in this series of compounds.

EXPERIMENTAL

General Considerations

Optical rotations were measured on a Jasco DIP-370 digital polarimeter. Infrared spectra were recorded on a Nicolet MX-5 FTIR spectrometer. Gas chromatography was accomplished using a Hewlett-Packard Model 5890 instrument. Mass spectra were measured on a VG-70SE magnetic sector mass spectrometer. NMR spectra were measured on a General Electric QE-300 or a GN OMEGA 500 instrument. $^1$H NMR chemical shifts are reported in ppm with the chemical shift of the residual protons of the solvent used as internal standards. $^{13}$C NMR chemical shifts are reported in ppm by using the natural abundance $^{13}$C of the solvent as an internal standard. Ultraviolet spectra were recorded on a Hewlett-Packard Model 8452A diode array spectrophotometer. All solvents were distilled from glass before use.

Two hundred sacoglossans (*Elysia rufescens*), were collected at Black Point, O'ahu during April and May 1992, and extracted 3 times with EtOH. Spring appears to be the time of year *Elysia rufescens* is in greatest abundance at Black Point. The combined extracts were then chromatographed using silica gel flash chromatography (hexane, hexane/EtOAc (1:1), EtOAc, EtOAc/MeOH (1:1), MeOH, MeOH/HOAc (98:2). The depsipeptides were found in the EtOAc/MeOH (1:1) fraction. Repeated HPLC RP18 MeCN/H$_2$O/TFA (55/45/1)—MeCN/H$_2$O/TFA ((30/70/1) yielded six new depsipeptides.

KAHALALDDE F

Final purification was accomplished by HPLC on RP18 MeCN/H$_2$O/TFA (55/45/1). Physical data: [α]D-8°(c 4.32, MeOH); $^1$H NMR (500 MHz, TFA/DMF); amino acid unit, δ (carbon position, mult, J): Val-1 4.16 (2, t, J=9.0 Hz), 7.11 (NH on 2, d, J=8.9 Hz), 1.77 (3, m), 0.95 (4, m), 0.95 (5, m); Dhb 9.20 (NH on 2, s), 6.48 (3, q, J=6.9 Hz), 1.43 (4, d, J=6.6 Hz); Phe 4.68 (2, q, J=6.6 Hz), 8.62 (NH on 2, d, J=6.6 Hz), 3.2 (3, dd, J=13.7, 7.2 Hz), 3.0 (3, dd, J=13.7, 9.0 Hz), 7.32 (5, d, J=7.2 Hz), 7.28 (6, t, J=7.5 Hz), 7.21 (7, t, J=7.2 Hz); Val-2 4.36 (2, m), 7.82 (NH on 2, d, J=6.6 Hz), 2.12 (3, m), 0.85 (4, m), 0.77 (5, d, J=6.6 Hz); Ileu-1 4.53 (2,m), 8.38 (NH on 2, d, J=9.6 Hz), 1.98 (3, m), 0.92 (4, d, J=6.6 Hz), 1.40 (5, m), 1.13 (5, m), 0.88 (6, t, J=7.2 Hz); Thr-1 4.63 (2, t, J=9.3 Hz), 8.12 (NH on 2, d, J=5.7), 5.07 (3, dq, 9.6, 6.0 Hz), 1.18 (4, d, J=6.3 Hz); Ileu-2 4.52 (2, m), 7.72 (NH on 2, d, J=8.4 Hz), 1.88 (3, m), 0.88 (4, d, J=6.3 Hz), 1.40 (5, m), 1.13 (5, m), 0.88 (6, d, J=7.2 Hz); Orn 4.48 (2, m), 7.92 (NH on 2, d, J=7.8 Hz), 1.76 (3, m), 1.83 (4, m), 3.10 (5, p, J=5.1 Hz); Pro 4.42 (2, m), 2.12 (3, m), 2.02 (4, m), 1.88 (4, m), 3.75 (5, m), 3.68 (5, m); Val-3 4.41 (2, m), 7.90 (NH on 2, d, J=7.2 Hz), 2.12 (3, m), 0.95 (4, m), 0.85 (5, m); Val-4 4.34 (2, m), 7.68 (NH on 2, d, J=8.1 Hz), 2.17 (3, m), 0.95 (4, m), 0.90 (5, m); Thr-2 4.46 (2, m), 7.77 (NH on 2, d, J=8.1), 4.21 (3, dq, 6.3, 3.6 Hz), 1.12 (4, d, J=6.6); Val-5 4.32 (2, m), 7.85, (NH on 2, d, J=8.1 Hz), 7.82 (NH on (second conformation), d, J=8.1 Hz), 2.14 (3, m), 0.95 (4, m), 0.90 (5, m); 5-MeHex 2.26 (2, m), 1.60 (3, m), 1.20 (4, m), 1.55 (5, m), 0.87 (6, d, J=7.2 Hz), 0.87 (7, d, J=7.2 Hz); 5-MeHex 2.29 (2,m), 1.65 (3, m), 1.40 (3, m), 1.13 (4, m), 1.35 (5, m), 0.90 (6, m), 0.90 (7, m); $^{13}$C NMR (125 MHz TFA/DMF): amino acid unit, δ (carbon position); Val-1 70.40 (1), 60.31 (2), 30.75 (3), 19.58 (4), 18.76 (5); Dhb 164.54 (1), 130.30 (2), 131.26 (3), 12.68 (4); Phe 171.31 (1), 56.27 (2), 36.79 (3), 138.23 (4), 129.86 (5), 128.77 (6), 126.98 (7); Val-2 172–94 (1), 58.57 (2), 32.38 (3), 18.92 (4), 17.60 (5); Ileu-1 171.87 (1), 57.48 (2), 38.78 (3), 14.56 (4), 26.78 (5), 11.67; Thr-1 169.68 (1), 57.37 (2), 71.05 (3), 17.34 (4); Ileu-2 171.92 (1), 57.29 (2), 38.01 (3), 14.78 (4), 26.55 (5), 11.63 (6); Orn 172.01 (1), 52.87 (2), 29.63 (3), 24.39 (4), 40.05 (5); Pro 172.55 (1), 60.23 (2), 29.58 (3), 25.38 (4), 48.03 (5); Val-3 171.28 (1), 57.57 (2), 30.54(3), 19.61 (4), 18.80 (5); Val-4 171.83 (1), 59.10 (2), 31.26 (3), 19.45 (4), 18.08 (5); Thr-2 170.97 (1), 58.89 (2), 67.36 (3), 19.66 (4); Val-5 172.67 (1), 59.64 (2), 30.66 (3), 19.61 (4), 18.43 (5), 5-MeHex 173.83 (1), 36.28 (2), 23.99 (3), 38.96 (4), 28.10 (5), 22.54 (6), 22.50 (7); 5-MeHex (second conformation) 174.08 (1), 33.86 (2), 32.84 (3), 29.75 (4), 34.54 (5), 19.51 (6), 11.20 (7); IR neat (NaCl): 3287 (s, br), 2964 (s, br), 1646 (s), 1528 (s), 1465 (s), 1388 (m), 1228 (m), cm$^{-1}$; mass spectrum HRFAB m/z (fragment, %) 1477.9408 (M$^+$+1, 85)(calcd for C$_{75}$H$_{125}$N$_{14}$O$_{16}$: 1477.9398); UV (MeOH): λ$_{max}$ 204 (89,630)nm.

Amino acid analysis by GC-MS with a Chirasil-Val column indicates that Kahalalide F consists of 2 D-Ileu, -Orn, L-Phe, D-Pro, L-Thr, D-Allo-Thr, 3 D-Val and 2 L-Val.

TABLE II $^1$H and $^{13}$C NMR Data for Kahalalide F (I) in DMF/TFA

| Amino Acid | Carbon | $^{13}$C, ppm$^a$ | Mult. | $^1$H, ppm$^b$ | Multiplicity |
|---|---|---|---|---|---|
| Valine-1 | 1 | 170.4 | s | (NH) 7.11 | d, J=8.9 |
| | 2 | 60.3 | d | 4.16 | t, J=9.0 |
| | 3 | 30.8 | d | 1.77 | m |
| | 4 | 19.6 | q | 0.95 | m |
| | 5 | 18.8 | q | 0.95 | m |
| Dehydroamino butyric acid | 1 | 164.5 | s | (NH) 9.20 | s |
| | 2 | 130.3 | s | | |
| | 3 | 131.3 | d | 6.48 | q, J=6.9 |
| | 4 | 12.7 | q | 1.43 | d, J=6.6 |
| Phenylalanine | 1 | 171.3 | s | (NH) 8.62 | d, J=6.6 |
| | 2 | 56.3 | d | 4.68 | q, J=6.6 |
| | 3 | 36.8 | t | 3.23 | dd, J=13.7, 7.2 |
| | | | | 3.00 | dd, J=13.7, 9.0 |
| | 4 | 138.2 | s | | |
| | 5, 5' | 129.9 | d | 7.32 | d, J=7.2 |
| | 6, 6' | 128.8 | d | 7.28 | t, J=7.5 |
| | 7 | 127.0 | d | 7.21 | t, J=7.2 |
| Valine-2 | 1 | 172.9 | s | (NH) 7.82 | d, J=6.6 |
| | 2 | 58.6 | d | 4.36 | m |
| | 3 | 32.4 | d | 2.12 | m |
| | 4 | 18.9 | q | 0.85 | m |
| | 5 | 17.6 | q | 0.77 | d, J=6.6 |
| Isoleucine-1 | 1 | 171.9 | s | (NH) 8.38 | d, J=9.6 |
| | 2 | 57.5 | d | 4.53 | m |
| | 3 | 38.8 | d | 1.98 | m |
| | 4 | 14.6 | q | 0.92 | d, J=6.6 |
| | 5 | 26.8 | t | 1.40, 1.13 | m,m |
| | 6 | 11.7 | q | 0.88 | t, J=7.2 |
| Threonine-1 | 1 | 169.7 | s | (NH) 8.12 | d, J=5.7 |
| | 2 | 57.4 | d | 4.63 | t, J=9.3 |
| | 3 | 71.1 | d | 5.07 | dq, J=9.6, 6.0 |
| | 4 | 17.3 | q | 1.18 | d, J=6.3 |
| Isoleucine-2 | 1 | 171.9 | s | (NH) 7.72 | d, J=8.4 |
| | 2 | 57.3 | d | 4.52 | m |
| | 3 | 38.0 | d | 1.88 | m |
| | 4 | 14.8 | q | 0.88 | d, J=6.3 |
| | 5 | 26.6 | t | 1.40, 1.13 | m, m |
| | 6 | 11.6 | q | 0.88 | t, J=7.2 |
| Ornithine | 1 | 172.0 | s | (NH) 7.92 | d, J=7.8 |
| | 2 | 52.9 | d | 4.48 | m |
| | 3 | 29.6 | t | 1.76 | m |
| | 4 | 24.4 | t | 1.83 | m |
| | 5 | 40.1 | t | 3.10 | p, 5.1 |
| Proline | 1 | 172.6 | s | | |
| | 2 | 60.2 | d | 4.42 | m |
| | 3 | 29.6 | t | 2.12, 1.97 | m, m |
| | 4 | 25.4 | t | 2.02, 1.88 | m, m |
| | 5 | 48.0 | t | 3.75, 3.68 | m, m |
| Valine-3 | 1 | 171.3 | s | (NH) 7.90 | d, J=7.2 |
| | 2 | 57.6 | d | 4.41 | m |
| | 3 | 30.5 | d | 2.12 | m |
| | 4 | 19.6 | q | 0.95 | m |
| | 5 | 18.8 | q | 0.85 | m |
| Valine-4 | 1 | 171.8 | s | (NH) 7.68 | d, J=8.1 |
| | 2 | 59.1 | d | 4.34 | m |
| | 3 | 31.3 | d | 2.17 | m |
| | 4 | 19.5 | q | 0.95 | m |
| | 5 | 18.1 | q | 0.90 | m |
| Threonine-2 | 1 | 171.0 | s | (NH) 7.77 | d, J=8.1 |
| | 2 | 58.9 | d | 4.46 | m |
| | 3 | 67.4 | d | 4.21 | dq, J=6.3, 3.6 |

TABLE II-continued

¹H and ¹³C NMR Data for Kahalalide F (I) in DMF/TFA

| Amino Acid | Carbon | ¹³C, ppm[a] | Mult. | ¹H, ppm[b] | Multiplicity |
|---|---|---|---|---|---|
| | 4 | 19.7 | q | 1.12 | d, J=6.6 |
| Valine-5 | 1 | 172.7 | s | (NH) | d, J=8.1 |
| | | conf. #2 | | 7.85, | d, J=8.1 |
| | | | | (NH) 7.82 | |
| | 2 | 59.6 | d | 4.32 | m |
| | 3 | 30.7 | d | 2.14 | m |
| | 4 | 19.6 | q | 0.95 | m |
| | 5 | 18.4 | q | 0.90 | m |
| 5-Methyl- | 1 | 173.8 | s | | |
| Hexanoic acid | 2 | 36.3 | t | 2.26 | m |
| | 3 | 24.0 | t | 1.60 | m |
| | 4 | 39.0 | t | 1.20 | m |
| | 5 | 28.1 | d | 1.55 | m |
| | 6 | 22.5 | q | 0.87 | d, J=7.2 |
| | 7 | 22.5 | q | 0.87 | d, J=7.2 |
| 5-Methyl- | 1 | 174.1 | s | | |
| Hexanoic acid | 2 | 33.9 | t | 2.29 | m |
| (second | 3 | 32.8 | t | 1.65, 1.40 | m |
| conformation) | 4 | 29.8 | t | 1.13 | m |
| | 5 | 34.5 | d | 1.35 | m |
| | 6 | 19.5 | q | 0.90 | m |
| | 7 | 11.2 | q | 0.90 | m |

[a] at 125 MHz, DMF signal at 35.2 ppm;
[b] at 500 MHz, DMF signal at 2.91 ppm.

TABLE I

In vitro Activity of Kahalalide F from *Elysia rufescens* Assay (M.I.C. μg/mL)

| Cytoxicity μg/mL (IC50) | |
|---|---|
| A-549 | 2.5 |
| HT-29 | 0.25–0.5 |
| Antiviral μg/mL (% reduction) | |
| Mv 1 Lu/HSV II | 0.5 (95%) |
| CV-1/HSV-1 | >8 |
| BHK/VSV | >8 |
| Antifungal 6 mm disk | 50 μg/disk |
| *Aspergillus oryzae* | 19 mm |
| *Penicillium notatum* | 26 mm |
| *Tricophyton mentagrophy* | 34 mm |
| *Saccharomyces cerevisiae* | neg |
| *Candida albicans* | 16 mm |

We claim:

1. A substially pure compound Kahalalide F, said compound hag a molecular formula of $C_{75}H_{124}N_{14}O_{16}$, and consisting of five valines, two isoleucines, two threonines, ornithine, dehydroaminobutynic acid, proline, phenylalanine and 5-methylhexanoic acid; said compound further exhibiting the following physical and chemical properties: $[\alpha]_D$ -8° (c 4.32, MeOH; ¹H NMR (500 MHz, TFA/DMF); amino acid unit, δ (carbon position, mult, J): Val-1 4.16 (2, t, J=9.0 Hz), 7.11 (NH on 2, d, J=8,9 Hz), 1.77 (3, m), 0.95 (4, m), 0.95(5, m), Dhb 9.20 (NH on 2, s), 6.48 (3, q, J=6.9 Hz), 1.43 (4, d, J=6.6 Hz); Phe 4.68 (2, q, J=6.6 Hz), 8.62 (NH on 2, d, J=6.6 Hz), 3.2 (3, dd, J=13.7, 7.2 Hz), 3.0 (3, dd, J=13.7, 9.0 Hz), 7.32 (5, d, J=7.2 Hz), 7.28 (6, t J=7.5 Hz), 7.21 (7, t, J=7.2 Hz); Vol-2 4.36 (2, m), 7.82 (NH on 2, d, J=6.6 Hz), 2.12 (3, m), 0.85 (4, m), 0.77 (5, d, J=6.6 Hz); Ileu-1 4.53 (2, m), 8.38 (NH on 2, d, J=9.6 Hz), 1.98 (3, m), 0.92 (4, d, J=6.6 Hz), 1.40 (5, m), 1.13 (5, m), 0.88 (6, t, J=7.2 Hz); Thr-1 4.63 (2, t, J=9.3 Hz), 8.12 (HN on 2, d, J=5.7), 5.07 (3, dq, 9.6, 6.0 Hz), 1.18 (4, d, J=6.3 Hz); Ilue-2 4.52 (2, m), 7.72 NH on 2, d, J=8.4 Hz), 1.88 (3, m), 0.88 (4, d, J-6.3 Hz), 1.40 (5, m) 1.13 (5, m), 0.88 (6d, J=7.2 Hz) Orn 4.48 (2, m), 7.92 (NH on 2, d, J=7.8 Hz), 1.76 (3, m), 1.83 (4, m), 3.10 (5, p, J=5.1 Hz); Pro 4.42 (2, m), 2.12 (3, m), 1.97 (3, m), 2.02 (4, m), 1.88 (4, m), 3.75 (5, m), 3.68 (5, m); Val-3 4.41 (2, m), 7.90 (NH on 2, d, J=7.2 Hz), 2.12 (3, m), 0.95 (4, m), 0.85 (5, m); Val-4 4.34 (2, m), 7.68 (NH on 2, d, J=8.1 Hz), 2.17 (3, m), 0.95 (4, m), 0.90 (5, m); Thr-2 4.46 (2, m), 7.77 (NH on 2, d, J=8.1Hz), 4.21 (3, dq, 6.3, 3.6 Hz), 1.12 (4, d, J=6.6 Hz); Val-5 4.32 (2, m), 7.85, (HN on 2, d, J=8.1 Hz), 7.82 (NH on (second conformation), d, J=8.1 Hz), 2.14 (3, m), 0.95(4, m), 0.90 (5, m); 5-MeHex 2.26 (2, m), 1.60 (3, m), 1.20 (4, m), 1.55 (5, m), 0.87 (6, d, J=7.2 Hz), 0.87 (7, d, J=72 Hz); 5-MeHex 2.29 (2, m), 1.65 (3, m), 1.40 (3, m), 1.13 (4, m),1.35 (5, m), 0.90 (6, m), 0.90 (7, m); ¹³C NMR (125 MHz TFA/DMF): amino acid unit, δ (carbon position); Val-1 170.40 (1), 60.31 (2), 30.75 (3), 19.58 (4), 18.76 (5); Dhb 164.54 (1), 130.30 (2), 131.26 (3), 126.6 (4); Phe 171.31 (1), 56.27 (2), 36.79 (3), 138.23 (4), 129.86 (5), 128.77 (6), 126.98 (7); Val-2 172.94 (1), 58.57 (2), 32.38 (3), 18.92 (4), 17.60 (5);Ileu-1 171.87 (1), 57.48 (2), 38.78 (3), 14.56 (4), 26.78 (5), 11.67; Thr-1 169.68 (1), 57.37 (2), 71.05 (3), 17.34 (4); Ileu-2 171.92 (1), 57.29 (2), 38.01 (3), 14.78 (4), 26.55 (5), 11.63 (6); Orn 172.01 (1), 52.87 (2), 29.63 (3), 24.39 (4), 40.05 (5); Pro 172.55 (1), 60.23 (2), 29.58 (3), 25.38 (4), 48.03 (5); Val-3 171.28 (1), 57.57 (2), 30.54 (3), 19.61 (4), 18.80 (5); Val-4 171.83 (1), 59.10 (2), 31.26 (3), 19.45 (4), 18.08 (5); thr-2 170.97 (1), 58.89 (2), 67.36 (3), 19.66 (4); Val-5 172.67 (1), 59.64 (2), 30.66 (3), 19.61 (4), 18.43 (5); 5-MeHex 173.83 (1), 36.28 (2), 23.99 (3), 38.96 (4), 28.10 (5), 22.54 (6), 22.50 (7); 5-MeHex (second conformation) 174.08 (1), 33.86 (2), 32.84 (3), 29.75 (4), 34.54 (5), 19.51 (6), 11.20 (7); IR neat (NaCl): 3287 (s, br), 2964 (s, br), 1646 (s), 1528 (s), 1464 (s), 1388 (m), 1228 (m), cm⁻¹; mass spectrum HRFAB m/z (fragment, %) 1477.9408 (M⁺+1, 85); UV (MeOH): $\lambda_{max}$ 204 (89,630) nm.

2. The compound Kahalalide F of claim 1, which further has the folowing non-stereospecific structure:

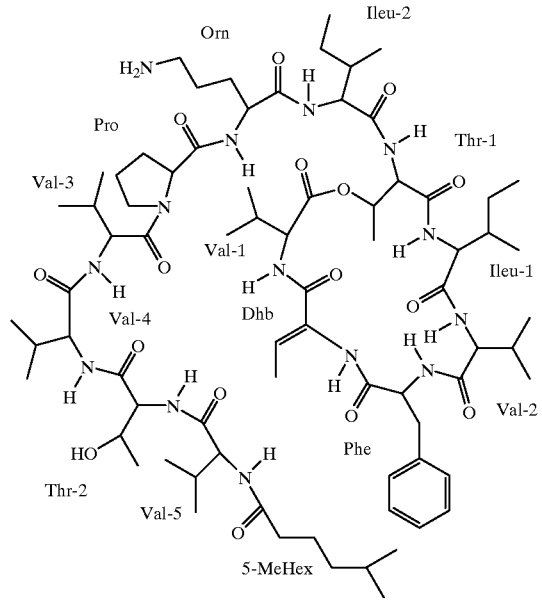

3. A pharmaceutical compostion comprising a pharmaceutical carrier or diluent and the substantially pure compound Kahalalide F, said compoumd having a molecular formula of $C_{75}H_{124}N_{14}O_{16}$, and conng of five valines, two isoleucines, two threonines, ornithine, dehydroamiobutyric acid, proline, phenylalanine and 5-methylhexoic acid; said compound further exhibiting the following physical and chemical properties:

$[\alpha]_D$ −8° (c 4.32, MEOH; $^1$H NMR (500 MHz, TFA/DMF); amino acid unit, δ (carbon position, mult, J): Val-1 4.16 (2, t, J=9.0 Hz), 7.11 (NH on 2, d, J=8,9 Hz), 1.77 (3, m), 0.95 (4, m), 0.95 (5, ma); Dhb 9.20 (NH on 2, s), 6.48 (3, q, J=6.9 Hz), 1.43 (4, d, J=6.6 Hz,); Phe 4.68 (2, q, J=6.6 HZ), 8.62 (NH on 2, d, J=6.6 Hz), 3.2 (3, dd, J=13.7, 7.2 Hz), 3.0 (3, dd, J=13.7, 9.0 Hz), 7.32 (5, d, J=7.2 Hz), 7.28 (6, t J=7.5 Hz), 7.21 (7, t, J=7.2 Hz); Val-2 4.36 (2, m), 7.82 (NH on 2, d, J=6.6 Hz), 2.12 (3, m), 0.85 (4, m), 0.77 (5, d, J=6.6 Hz); Ilue-1 4.53 (2, m), 8.38 (NH on 2, d, J=9.6 Hz), 1.98 (3, m), 0.92 (4, d, J=6.6 Hz), 1.40 (5, m), 1.13 (5, m), 0.88 (6, t, J=7.2 Hz); Thr-1 4.63 (2, t, J=9.3 Hz), 8.12 (NH on 2, d, J=5.7), 5.07 (3, dq, 9.6, 6.0 Hz), 1.18 (4, d, J=6.3 Hz); Ileu-2 4.52 (2, m), 7.72 (NH on 2, d, J=8.4 Hz), 1.88 (3, m), 0.88 (4, d, J-6.3 Hz), 1.40 (5, m) 1.13 (5, m), 0.88 (6, d, J=7.2 Hz) Orn 4.48 (2, m), 7.92 (NH on 2, d, J=7.8 Hz), 1.76 (3, m), 1.83 (4, m), 3.10 (5, p, J=5.1 Hz); Pro 4.42 (2, m), 2.12 (3, m), 1.97 (3, m), 2.02 (4, m), 1.88 (4, m), 3.75 (5, m), 3.68 (5, m); Val-3 4.41 (2, m), 7.90 (NH on 2, d, J=7.2 Hz), 2.12 (3, m), 0.95 (4, m), 0.85 (5, m); Val-4 4.34 (2, m), 7.68 (NH on 2, d, J=8.1 Hz), 2.17 (3, m), 0.95 (4, m), 0.90 (5, m); Thr-2 4.46 (2, m), 7.77 (NH on 2, d, J=8.1), 4.21 (3, dq, 6.3, 3.6 Hz), 1.12 (4, d, J=6.6 Hz); Val-5 4.32 (2, m), 7.85, (NH on 2, d, J=8.1 Hz), 7.82 (NH on (second conformation), d, J=8.1 Hz), 2.14 (3, m), 0.95 (4, m), 0.90 (5, m); 5MeHex 2.26 (2, m), 1.60 (3, m), 1.20 (4, m), 1.55 (5, m), 0.87 (6, d, J=7.2 Hz), 0.87 (7, d, J=7.2 Hz); 5MeHex 2.29 (2, m), 1.65 (3, m), 1.40 (3, m) 1.13 (4, m), 1.35 (5, m), 0.90 (6, m), 0.90 (7, m); $^{13}$C NMR (125 MHz TFA/DMF): amino acid unit, δ (carbon position); Val-1 170.40 (1), 60.31 (2), 30.75 (3), 19.58 (4), 18.76 (5); Dhb 164.54 (1), 130.30 (2), 131.26 (3), 12.68 (4); Phe 171.31 (1), 56–27 (2), 36.79 (3), 138.23 (4), 129.86 (5), 128.77 (6), 126.98 (7); Val-2 172.94 (1), 58.57 (2), 32.38 (3), 18.92 (4), 17.60 (5); Ileu-1 171.87 (1), 57.48 (2), 38.78 (3), 14.56 (4), 26.78 (5), 11.67; Thr-1 169.68 (1), 57.37 (2), 71.05 (3), 17.34 (4); Ileu-2 171.92 (1), 57.29 (2), 38.01 (3), 14.78 (4), 26.55 (5), 11.63 (6); Orn 172.01 (1), 52.87 (2), 29.63 (3), 24.39 (4), 40.05(5); Pro 172.35 (1), 60.23 (2), 29.58 (3), 25.38 (4), 48.03 (5); Val-3 171.28 (1), 57.57 (2), 30.54 (3), 19.61 (4), 18.80 (5); Val-4 171.83 (1), 59.10 (2), 31.26 (3), 19.45 (4), 18.08 (5); Thr-2 170.97 (1), 58.89 (2), 67.36 (3), 19.66 (4), 18.43 (5); Val-5 172.67 (1), 59.64 (2), 30.66 (3), 19.61 (4), 18.43 (5); 5-MeHex 173.83 (1), 36.28 (2), 23.99 (3), 38.96 (4), 28.10 (5), 22.54 (6), 22.50 (7); 5-MeHex (second conformation) 174.08 (1), 33.86 (2), 32.84 (3), 29.75 (4), 34.54 (5), 19.51 (6), 11.20 (7); IR neat (NaCl): 3287 (s, br), 2964 (s, br), 1646 (s), 1528 (s), 1464 (s), 1388 (m), 1228 (m), cm$^{-1}$; mass spectrum HRFAB m/z (fragment, %) 1477.9408 (M$^+$+1, 85); UV (MeOH): $\lambda_{max}$ 204 (89,630) nm.

4. The pharmaceutical composition of claim 3, wherein the compound Kahalalide F further has the folowing non-streospecific structure

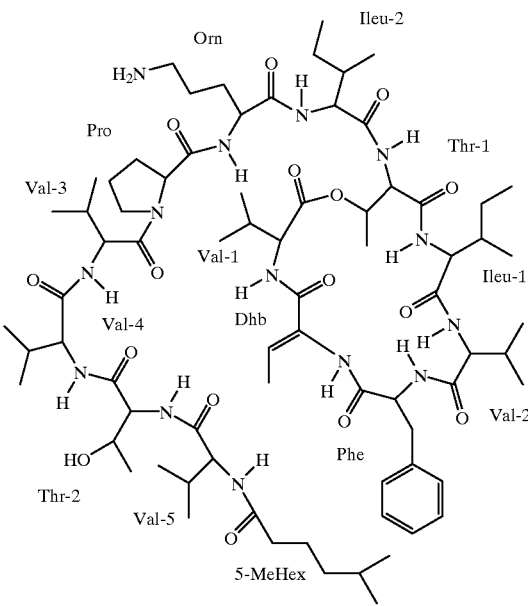

5. A method of treating fungal infections in mammals comprising administering to patient in need of such treatment, an amount of the substantially puxe compound Kahalalide F or a pharmaceutically acceptable salt thereof, sufficient to slow or stop the growth of the fungal infection; said compound having a molecula formula of $C_{75}H_{124}N_{14}O_{16}$, and consisting of five valines, two isoleucines, two theonines, ornithine, dehydroaminobutiric acid, proline, phenylalanie and 5-methylhexanoic acid; said compound further exhibiting the folowing physical and chemical properties:

$[\alpha]_D$ −8° (c 4.32, MEOH; $^1$H NMR (500 MHz, TFA/DMF); amino acid unit, δ (carbon position, mult, J): Val-1 4.16 (2, t, J=9.0 Hz), 7.11 (NH on 2, d, J=8,9 Hz), 1.77 (3, m), 0.95 (4, m), 0.95 (5, ma); Dhb 9.20 (NH on 2, s), 6.48 (3, q, J=6.9 Hz), 1.43 (4, d, J=6.6 Hz,); Phe 4.68 (2, q, J=6.6 HZ), 8.62 (NH on 2, d, J=6.6 Hz), 3.2 (3, dd, J=13.7, 7.2 Hz), 3.0 (3, dd, J=13.7, 9.0 Hz), 7.32 (5, d, J=7.2 Hz), 7.28 (6, t J=7.5 Hz), 7.21 (7, t, J=7.2 Hz); Val-2 4.36 (2, m), 7.82 (NH on 2, d, J=6.6 Hz), 2.12 (3, m), 0.85 (4, m), 0.77 (5, d, J=6.6 Hz); Ilue-1 4.53 (2, m), 8.38 (NH on 2, d, J=9.6 Hz), 1.98 (3, m), 0.92 (4, d, J=6.6 Hz), 1.40 (5, m), 1.13 (5, m), 0.88 (6, t, J=7.2 Hz); Thr-1 4.63 (2, t, J=9.3 Hz), 8.12 (NH on 2, d, J=5.7), 5.07 (3, dq, 9.6, 6.0 Hz), 1.18 (4, d, J=6.3 Hz); Ileu-2 4.52 (2, m), 7.72 (NH on 2, d, J=8.4 Hz), 1.88 (3, m), 0.88 (4, d, J-6.3 Hz), 1.40 (5, m) 1.13 (5, m), 0.88 (6, d, J=7.2 Hz) Orn 4.48 (2, m), 7.92 (NH on 2, d, J=7.8 Hz), 1.76 (3, m), 1.83 (4, m), 3.10 (5, p, J=5.1 Hz); Pro 4.42 (2, m), 2.12 (3, m), 1.97 (3, m), 2.02 (4, m), 1.88 (4, m), 3.75 (5, m), 3.68 (5, m); Val-3 4.41 (2, m), 7.90 (NH on 2, d, J=7.2 Hz), 2.12 (3, m), 0.95 (4, m), 0.85 (5, m); Val-4 4.34 (2, m), 7.68 (NH on 2, d, J=8.1 Hz), 2.17 (3, m), 0.95 (4, m), 0.90 (5, m); Thr-2 4.46 (2, m), 7.77 (NH on 2, d, J=8.1), 4.21 (3, dq, 6.3, 3.6 Hz), 1.12 (4, d, J=6.6 Hz); Val-5 4.32 (2, m), 7.85, (NH on 2, d, J=8.1 Hz), 7.82 (NH on (second conformation), d, J=8.1 Hz), 2.14 (3, m), 0.95 (4, m), 0.90 (5, m); 5MeHex 2.26 (2, m), 1.60 (3, m), 1.20 (4, m), 1.55 (5, m), 0.87 (6, d, J=7.2 Hz), 0.87 (7, d, J=7.2 Hz); 5MeHex 2.29 (2, m), 1.65 (3, m), 1.40 (3, m) 1.13 (4, m), 1.35 (5, m), 0.90 (6, m), 0.90 (7, m); $^{13}$C NMR (125 MHz TFA/DMF): amino acid unit, 6 (carbon position); Val-1 170.40 (1), 60.31 (2), 30.75 (3), 19.58 (4), 18.76 (5); Dhb 164.54 (1), 130.30 (2), 131.26 (3), 12.68 (4); Phe 171.31 (1), 56–27 (2), 36.79 (3), 138.23 (4), 129.86 (5), 128.77 (6), 126.98 (7); Val-2 172.94 (1), 58.57 (2), 32.38 (3), 18.92 (4), 17.60 (5); Ileu-1 171.87 (1), 57.48 (2), 38.78 (3), 14.56 (4), 26.78 (5), 11.67; Thr-1 169.68 (1), 57.37 (2), 71.05 (3), 17.34 (4); Ileu-2 171.92 (1), 57.29 (2), 38.01 (3), 14.78 (4), 26.55 (5), 11.63 (6); Orn 172.01 (1), 52.87 (2), 29.63 (3), 24.39 (4), 40.05(5); Pro 172.35 (1), 60.23 (2), 29.58 (3), 25.38 (4), 48.03 (5); Val-3 171.28 (1), 57.57 (2), 30.54 (3), 19.61 (4), 18.80 (5); Val-4 171.83 (1), 59.10 (2), 31.26 (3), 19.45 (4), 18.08 (5); Thr-2 170.97 (1), 58.89 (2), 67.36 (3), 19.66 (4); Val-5 172.67 (1), 59.64 (2), 30.66 (3), 19.61 (4), 18.43 (5); 5-MeHex 173.83 (1), 36.28 (2), 23.99 (3), 38.96 (4), 28.10 (5), 22.54 (6), 22.50 (7); 5-MeHex (second conformation) 174.08 (1), 33.86 (2), 32.84 (3), 29.75 (4), 34.54 (5), 19.51 (6), 11.20 (7); IR neat (NaCl): 3287 (s, br), 2964 (s, br), 1646 (s), 1528 (s), 1464 (s), 1388 (m), 1228 (m), cm$^{-1}$; mass spectrum HRFAB m/z (fragment, %) 1477.9408 (M$^+$+1, 85); UV (MeOH): $\lambda_{max}$ 204 (89,630) nm.

6. The method of treatment of claim 5, wherein compound Kahalalide F has the following non-stereospecific structure:

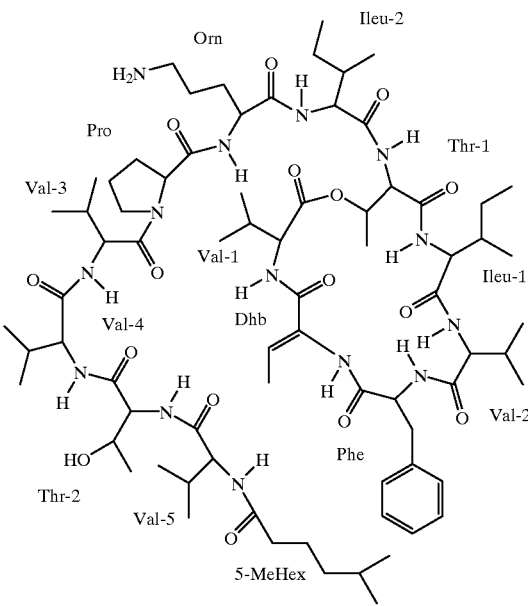

7. The method of claim 5, wherein the fungal infection is caused by *Aspergillus oryzae*.

8. The method of claim 5, wherein the fungal infection is caused by *Penicillium notatum*.

9. The method of claim 5, wherein the fungal infection is caused by *Trichophyton mentagrophy*.

10. The method of claim 5, wherein the fungal infection is caused by *Candida albicans*.

* * * * *